United States Patent [19]

Faryniarz et al.

[11] Patent Number: 4,740,370
[45] Date of Patent: Apr. 26, 1988

[54] PROCESS FOR PREPARING NAIL COATING COMPOSITIONS

[76] Inventors: Joseph R. Faryniarz, 78 Benz St., Ansonia, Conn. 06401; John S. Wooster, 2110 Nichols Ave., Stratford, Conn. 06497

[21] Appl. No.: 718,888

[22] Filed: Jun. 13, 1985

Related U.S. Application Data

[62] Division of Ser. No. 590,571, Mar. 16, 1984, abandoned.

[51] Int. Cl.$^4$ .............................................. A61K 7/04
[52] U.S. Cl. ..................................................... 424/61
[58] Field of Search ......................................... 424/61

[56] References Cited

U.S. PATENT DOCUMENTS

| | | | |
|---|---|---|---|
| 2,261,623 | 11/1941 | Hucks | 424/61 |
| 3,849,547 | 11/1974 | Kalopissis | 424/61 |
| 3,864,294 | 2/1975 | Busch, Jr. | 424/61 |
| 3,907,580 | 9/1975 | van Ham | 424/61 |
| 3,927,203 | 12/1975 | Seymour et al. | 424/61 |
| 4,097,589 | 6/1978 | Shansky | 424/61 |
| 4,126,675 | 11/1978 | Boulogne et al. | 424/61 |
| 4,179,304 | 12/1979 | Rossomando | 424/61 |
| 4,283,324 | 8/1981 | Duffy | 424/61 |
| 4,302,442 | 11/1981 | Socci et al. | 424/61 |

FOREIGN PATENT DOCUMENTS 2830958  2/1979  Fed. Rep. of Germany .

OTHER PUBLICATIONS

Kirk-Othmer Encyclopedia of Chemical Technology, Second Ed., vol. 6, pp. 368–370, 1965.
Cellofilm Corporation Technical Report-2 pages.
"Dispersed Pigment Chips" by L. C. Willsmer, *Paint, Oil and Colour Journal*, Feb. 22, 1963, pp. 399–401.
"Nitrocellulose and Organosoluble Cellulose Ethers in Coatings", *Federation Series on Coatings Technology*, Sep. 1972, Unit Twenty-One, pp. 12–15.
"Plasticizers", *Federation Series on Coatings Technology*, Apr. 1974, Unit Twenty-Two, pp. 88–91.
Chemical Abstracts, vol. 97, 1982, p. 368.
"Manicure Preparations", *Harry's Cosmeticology*, 1982, Seventh Edition, pp. 375–389.
A Manual of Cosmetic Analysis, Chapter 7, "Analysis of Nail Lacquers", p. 4.
Cosmetics Science and Technology, vol. 2, Chapter 29, pp. 521–539 and 689.

*Primary Examiner*—J. R. Brown
*Assistant Examiner*—Jacqueline M. Stone
*Attorney, Agent, or Firm*—Brumbaugh, Graves, Donohue & Raymond

[57] ABSTRACT

Nail polish compositions comprising pigment material, and film forming material, wherein the pigment material is present in amounts not less than about 2.0% by weight and said nail polish composition has a Newtonian viscosity not greater than about 600 cps.

17 Claims, 2 Drawing Sheets

PROCESS FOR PREPARING NAIL COATING COMPOSITIONS

This application is a division of application Ser. No. 590,571, filed on Mar. 16, 1984, and now abandoned.

BACKGROUND OF THE INVENTION

The present invention relates to novel high pigment/low viscosity nail polish compositions and a process for preparing the same.

Typical prior art processes for the preparation of pigments in a form suitable for use in nail polish compositions generally involve individually milling mixtures of a suitable pigment in alcohol wet cellulose nitrate and plasticizer to provide nitrocellulose-pigment chips. Such processes are generally known in the art as "chipping" and given the explosive property of nitrocellulose are both hazardous and limited to specialized milling techniques. More specifically, the prior art "chipping" process can only safely be carried out as long as the alcohol remains in intimate contact with the nitrocellulose in sufficient quantities to prevent the mixture from being ignited by the heat evolved during milling. As a practical consequence, the "chipping" process is inherently limited in the extent to which the pigment can be ground or milled. Moreover, the pigment chips produced in accordance with the prior art technology are highly flammable, thereby necessitating special shipping, storage and handling procedures.

Apart from the aforementioned problems, the utilization of the nitrocellulose-pigment chips in the manufacture of nail polish compositions presents other difficulties, principally due to the fact that the cellulose nitrate increases the viscosity of the final coating formula in direct proportion to the amount of pigment present therein. Compositions which utilize large amounts of pigment necessarily contain large amounts of cellulose nitrate, which in turn necessitate thinning in order to obtain a suitably brushable final product. Thinners, however reduce the pigment and polymer solids concentration and hence, their use is counter productive to obtaining a final product having acceptable coverage properties. Moreover, in preparing nail polish compositions, the nitrocellulose pigment chips generally require additional processing prior to incorporation into a suspension base lacquer, e.g., the chips must first be redissolved in a lacquer thinner to provide a solvent based paste. Change in pigment concentrations as a result of thinning, solvent loss or pigment settling are frequent problems encountered in the prior art techniques of preparing high quality nail polishes.

Other known techniques and equipment used in preparing suitable pigment dispersions (homogenizers, media mills (sand and ball mills) and colloid mills) require diluting the nitrocellulose grinding medium with flammable solvents in order to obtain a suitable viscosity. These processes suffer similar problems due to poor size control of the pigment particle; flammability; low percentage pigment concentrations due to viscosity considerations; and destruction of cellulose nitrate polymer molecule attributable to high-shear milling.

SUMMARY OF THE PRESENT INVENTION

It is an object of the present invention to overcome the aforesaid problems previously experienced and further provide for the manufacture of novel coating compositions and particularly nail polishes, having very high pigment loads, i.e. from about 2.0% to about 7.0% by weight and low viscosities, i.e. not greater than about 600 cps. Said compositions can be easily applied and exhibit all of the desired physical properties (gloss, hardness, flexibility, wear resistance) which are essential to a high-quality nail polish product. In accordance with the present invention, pigment shades are ground in a nitrocellulose-free mill base to provide a pigment paste which can be readily incorporated in a suitable suspension base lacquer to form a novel nail polish composition.

The mill base (pigment grinding medium) of the present invention is essentially non-flammable, non-explosive composition in which pigments can be readily milled (without the hazards associated with prior art techniques) on a wide variety of high-energy milling equipment to provide an optimum pigment particle size, which directly correlates with an excellent finished product gloss and improved particle suspension stability.

In accordance with the present invention, the mill base, while nitrocellulose-free, contains a suitable protective colloid to aid in preventing flocculation of the pigment particles. In selecting a suitable protective colloid, those skilled in the art will recognize that it should be compatible with the primary film forming agent to be used in the final lacquer formulation. The absence of cellulose nitrate in the mill base (and pigment composition derived from grinding the pigment in the mill base), permits the use of very high pigment levels in the finished coating product without appreciably increasing viscosity, thus providing a final product that not only can be easily applied to a desired surface but also has excellent coverage properties. Moreover, since cellulose nitrate, if present at all, is provided by way of a base lacquer formulation and not the mill base as in the prior art "chipping" technique, the potential for the destruction of the cellulose nitrate polymer molecule from the shear effects of high-energy processing techniques is eliminated and the resulting coating compositions exhibit excellent film properties.

Other significant advantages derived from the mill base of the present invention include the ability to directly formulate pigment paste compositions in a wide variety of shades, which can be easily incorporated into the final lacquer compositions without the costly, time-consuming and hazardous intermediate processing steps required with the prior art nitrocellulose-pigment chips.

Finally, as a result of the present invention, superior suspension stability is achieved in the nail polish compositions since a plurality of individual pigments can be ground together to provide a desired shade rather than combining individually ground pigment shades. Co-ground pigments (generally) remain in suspension longer than pigments which are individually ground and combined to provide a desired shade. These and other advantages result from the present invention which is described in detail hereinbelow.

DETAILED DESCRIPTION OF THE INVENTION

Figure 1:
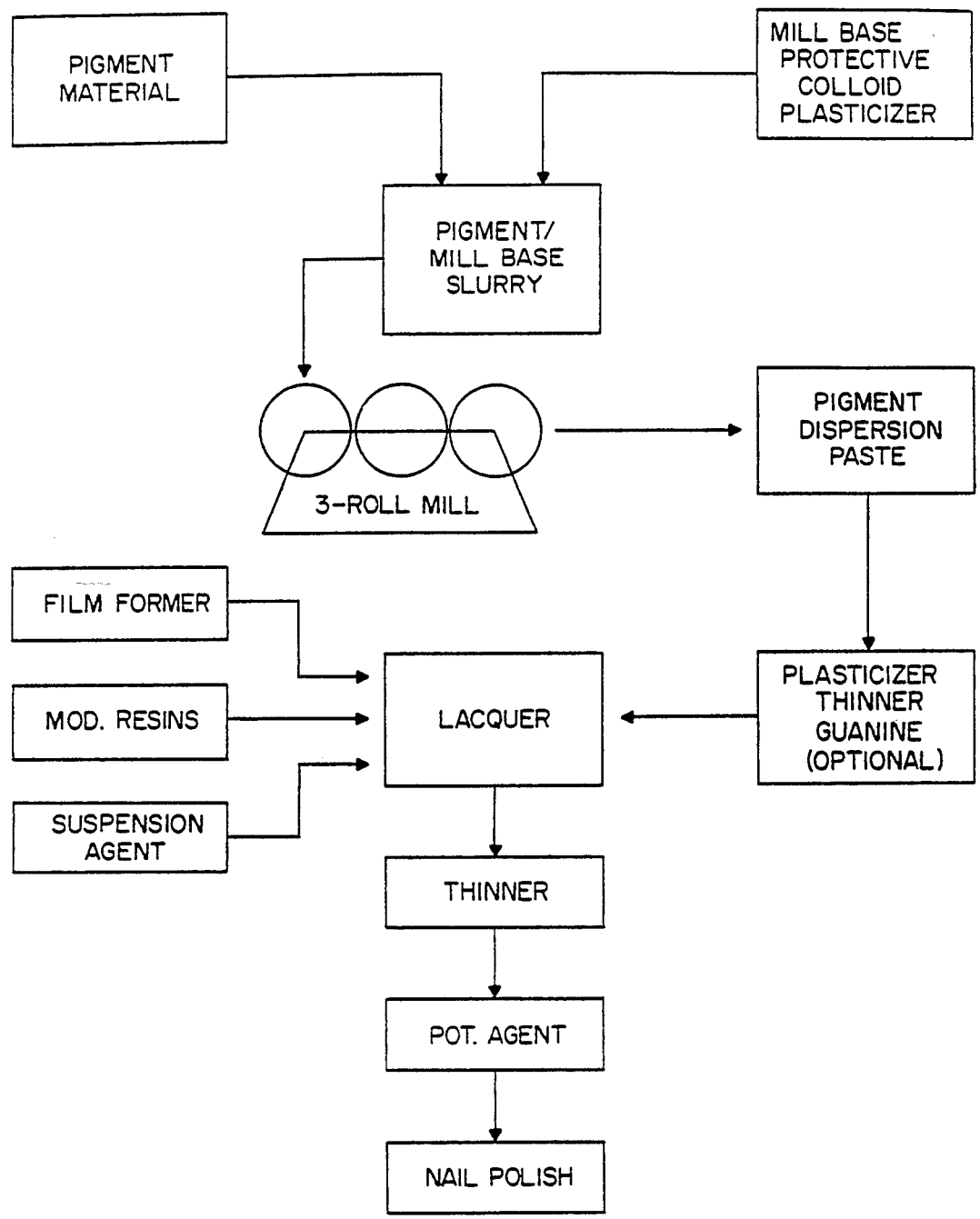
FIG. 1 is a flow diagram illustrating the sequence of processing steps utilized in the preparation of the pigment paste and final nail lacquer compositions made therefrom.
Figure 2:
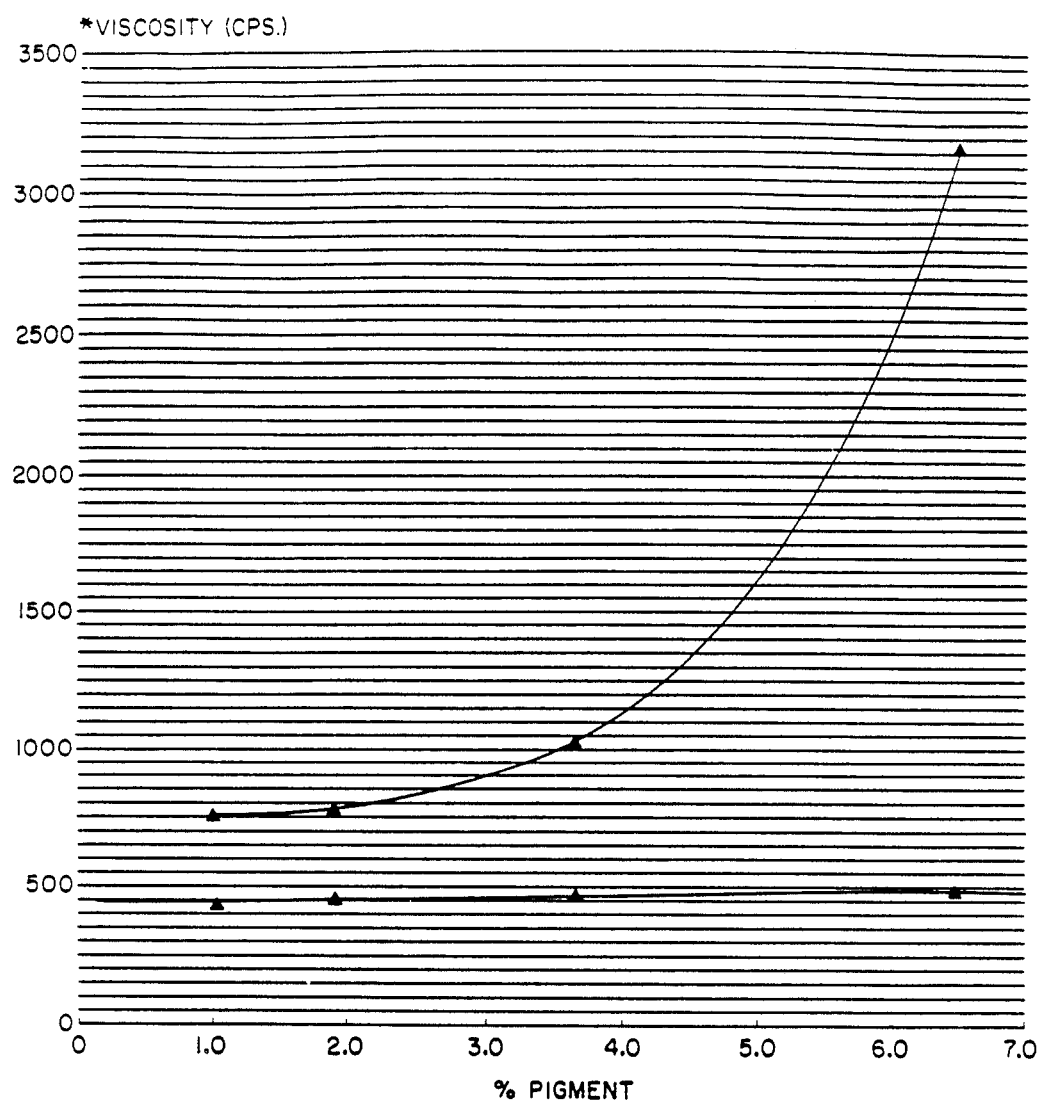
FIG. 2 is a graph which plots the viscosity/% pigment data taken from Table 2.

Suitable pigments for use in the mill base include all those known and conventionally used in the cosmetic industry, and hence they should be non-toxic, non-sensitizing, non-staining, substantially insoluble in solvents, free from any tendency to bleed, compatible with solvents used in the final lacquer formulation and moderately stable to light. The average particle size of the selected pigment should be very small, i.e. from about 0.1 microns to about 2.0 microns to insure satisfactory dispersing properties.

As a practical matter, pigments used in nail polish must conform to appropriate national legislation, which in the United States means that the pigment or colorant must be certified by the Food and Drug Administration (FDA). The most widely used pigments include the following: D&C Red 6, D&C Red 30, D&C Red 36, D&C Red 9, D&C Red 7, D&C Red 21, D&C Red 34, FD&C Yellow 5, FD&C Yellow 6, D&C Ferric Blue F, and cosmetic iron oxides. In addition to the foregoing, titanium dioxide is frequently used as a pigment in combination with other pigments, primarily to impart opacity and to produce pale, finished pigment shades.

Pigments may be ground individually as well as in combination to produce a desired pigment shade. The amount of pigment ingredient utilized may range from about 20.0% to about 80.0%. However, one skilled in the art will recognize that the amount of pigment incorporated into the mill base will depend on the specific properties of the pigment or pigments utilized, e.g. density and oil absorption, as well as the viscosity of the combined mill base and pigment and the need to adjust the pigment percentage to accomodate the processing equipment requirements.

In accordance with the present invention, the pigment (or pigments) selected for use is ground in a mill base formulation to provide a paste composition which may be directly incorporated, without additional processing, into a lacquer formulation to provide a finished coating composition, e.g. nail polish.

The essential components of the mill base, into which the pigment is ground, comprise (1) a water-insoluble protective colloid capable of preventing flocculation of the pigment particles and which is compatible with the film former, present in the final coating composition; and (2) a plasticizer, having low volatility and which is both compatible with the protective colloid in the mill base as well as the film former used in the final coating composition. The mill base must be essentially non-flammable and non-explosive and which, when combined with the pigment and plasticizer, will provide a composition having a consistency suitable to permit grinding on high shear equipment. The resultant pigment paste composition, i.e. finely ground pigment in combination with the mill base ingredients, should be easily dispersable in a base lacquer composition without substantially affecting (increasing) the viscosity of the finished coating product.

The protective colloid utilized in the mill base should be sufficiently soluble in the plasticizer used therein and the concentration (amount) of the protective colloid should be adequate to provide enough material to completely coat the dispersed, individual pigment particles with at least a monomolecular layer. The molecular weight of the colloid should be sufficiently high in order to provide an adequate colloidal effect to prevent the pigment particles from agglomerating or flocculating. Moreover, the colloid chosen should be compatible with cellulose nitrate or other desired film forming agents present in the final lacquer composition.

While the foregoing are the primary criteria for selecting a suitable protective colloid, it is also important that it be soluble in the solvent system used in the finished product and not appreciably increase the viscosity of the finished product, i.e. to a degree which unacceptably reduces the brushability of the final product. Other considerations which should be taken into account in selecting a suitable protective colloid include: its stability in the final formulation; its suitability for end use, i.e. innocuous to surfaces to which the finished coating composition is to be applied, e.g. fingernails; its effect on properties of final coating composition, e.g. gloss, adhesion, resistance to environmental conditions, depth of finish, flexability and hardness of the film coating.

Representative chemical groups of suitable protective colloids include: saccharide based polymers, acrylic polymers, polyesters, alkyd resins, polyamides, cellulosic polymers, sulfonated naphthalenes, vinyl polymers, formaldehyde condensates, polyurethanes, substituted pyrrolidone polymers, and polypropylene oxides. Preferred protective colloids for use in the mill base of the present invention include toluene sulfonamideformaldehyde condensates (for example Monsanto's SANTOLITE MHP), methyl-butyl methacrylate copolymer (Rohm & Haas' Acryloid B-66"), sucrose benzoate, ethyl cellulose, dimer acid based polyamide resin (Henkel's Versamide 940) and polymeric esterified pentaerythritol (Hercules' Herco-Flex 900).

Generally, the amount of protective colloid utilized in the mill base is that which is necessary to prevent agglomeration or flocculation of the pigment particles. It has been found that acceptable results are achieved when the protective colloid is present in amounts ranging from about 2.0% to about 25.0% by weight.

The selection of the plasticizer component used in the mill base of the present invention should be based on the following general criteria: its low volatility; its ability to sufficiently solubilize the chosen protective colloid; its compatibility with the chosen film former and other ingredients in the final lacquer formulation for the finished product; its ability not to appreciably increase the viscosity of the finished product; its suitability for the desired end use, e.g. dermatologically innocuous; its ability to impart improved properties to the finished product, e.g. flexibility and adhesion, color fastness and stability.

Within these general parameters, those skilled in the art will readily recognize suitable plasticizers among the following chemical groups: abietic acid derivatives, acetic acid derivatives, adipic acid derivatives, azelaic acid derivatives, benzoic acid derivatives, polyphenyl derivatives, citric acid derivatives, epoxy derivatives, proprietary esters, ether derivatives, formal derivatives, glutaric acid derivatives, glycerol derivatives, glycol derivatives, linear dibasic acid derivatives, petroleum derivatives, isobutyric acid derivatives, isophthalic acid derivatives, lauric acid derivatives, mellitates, myristic acid derivatives, nitrile derivatives, oleic acid derivatives, palmitic acid derivatives, paraffin derivatives, pelargonic acid derivatives, pentaerythritol derivatives, phosphoric acid derivatives, phthalic acid derivatives, polyesters, ricinoleic acid derivatives, sebacic acid derivatives, stearic acid derivatives, styrene derivatives, sucrose derivatives, sulfonic acid derivatives, terephthalic acid derivatives, and tartaric acid derivatives.

Preferred plasticizers include N-ethyl toluene sulfonamide (Santicizer 8), butyl benzyl phthalate (Santicizer S160) and tricresyl phosphate.

While the amount of plasticizer utilized in the mill base should be sufficient to solubilize the protective colloid, it genrally has been found that an amount ranging from about 75% to about 98% by weight is effective.

Surfactants may be optionally included in the mill base to aid pigment dispersion. When present, the amount of surfactant ranges from about 0.1% to about 5.0%; the preferred range being from 1.5% to about 3.0%. While any surfactant compatible with the ingredients in finished composition may be utilized, Byk-Mallinkrodt's "Anti-Terra-U" has been found to produce acceptable results.

Unlike the prior art "chipping" process, which yields a brittle pigment chip which must be further processed, i.e. dissolved in a solvent, prior to its incorporation into a base lacquer, the process of the present invention provides a pigment composition having a paste-like consistency which may be directly incorporated into the base lacquer formulation. Furthermore, the combined pigment and mill base composition of the present invention can be processed (milled) under high-shear conditions to provide a pigment paste composition wherein the average particle size of the pigment is in the range of about 0.1 microns to about 2.0 microns.

The following examples are illustrative of procedures which have been found useful for the preparation of specific mill bases and pigment compositions made in accordance with the present invention.

EXAMPLE 1

A two hundred pound batch of mill base was prepared in accordance with the following procedure. 159 lbs. (79.5% by weight) of plasticizer, (Santicizer 8), i.e., N-ethyl toluene sulfonamide was weighed out on a Toledo floor scale and poured into a steam-jacketed kettle equipped with a "Lightenin" variable-speed, propeller mixer. The plasticizer was heated to a temperature of 190° F. while being stirred. 41 lbs. (20.5% by weight) of protective colloid (Santolite MHP), i.e., toluene sulfonamideformaldehyde condensate was weighed out on a Toledo floor scale and broken into small pieces, the approximate diameters of which were no greater than about 1". The mixer speed was then increased to a point just prior to splashing and the protective colloid was slowly added to the plasticizer, the temperature of which was maintained at 170° F. until all of the protective colloid was dissolved. Thereafter, the mixture was cooled to and maintained at a temperature of between 120° to 140° F.

EXAMPLE 2

The procedure of Example 1 is repeated in the preparation of 50 lb. batches of each of the following mill base formulations:

| Ingredients | |
|---|---|
| (A) Santicizer 160 | 95.0% by weight |
| Acryloid B66 (Rohm & Hass) | 5.0% by weight |
| (B) Santicizer 8 | 97.0% by weight |
| Versamide 940 (Henkel Chemicals) | 3.0% by weight |
| (C) Santicizer 8 | 85.0% by weight |
| Sucrose Benzoate (Velsicol Prod.) | 15.0% by weight |

| Ingredients -continued | |
|---|---|
| (D) Tricresyl Phosphate (Monsanto) | 96.0% by weight |
| Ethyl Cellulose (Hercules Chemicals) | 4.0% by weight |
| (E) Tricresyl Phosphate (Monsanto) | 93.0% by weight |
| Herco Flex 900 Polyester (Hercules Chem.) | 7.0% by weight |

The following general procedure was used in preparing the pigment paste compositions of Examples 4–13.

EXAMPLE 3

An amount of mill base, prepared in accordance with Example 1, is placed into a change-can-paste mixer, the temperature of the mill base being between 120° F. to 140° F. A desired pigment shade is determined and appropriate amounts of an individual or plurality of pigments is weighed out and hand stirred into the mill base to prevent excessive dusting. The change-can, containing the pigment and mill base is placed under the mixer and mixed until a well dispersed slurry, completely free of lumps or dry pigment, is obtained. The milling equipment, i.e. a Buehler SDX-600 three-roll mill having standardized roller speeds, is prepared for operation by preheating the rolls to temperatures ranging from about 72° F. to about 124° F.; setting the hydraulic pressure of the rolls in a range from about 15 to 18.5 Bars (about 220 lbs. to about 272 lbs); and setting the hydraulic pressure of the knife at 7 Bars (about 103 lbs.). The slurry in the change can is then transferred to the mill and milled by passing the material through the mill a sufficient number of times at the specific parameters necessary to obtain a paste having the desired average pigment particle size, i.e. from about 0.1 to about 2.0 microns. Slurry material which does not pass through the mill rolls, i.e. "hang-back" material, is moistened with additional amounts of the slurry sufficient to enable it to pass through the rolls. Thereafter, the milled pigment paste is transferred to a clean change-can-paste mixer and mixed until uniform.

EXAMPLE 4

In accordance with the procedure of Example 3, a 2300 gram batch of a pigment paste composition was prepared using:

| | |
|---|---|
| Mill Base (Example 1) | 62.5% by weight |
| D & C Red #7 Calcium Lake | 37.5% by weight |

The three rolls of the Buehler SDX-600 mill were preheated to 99° F. and then rolls 1 and 3 were cooled to 97° F. The hydraulic roll pressure was set at 18.5 Bars (272 lbs.). The hydraulic knife pressure was set a 7 Bars (103 lbs.). The pigment slurry was passed through the mill three times at the above conditions and the resulting pigment paste composition was found to have an average particle size ranging from about 0.1 to about 2.0 microns as measured by Precision's grind gauge (N.I.P.I.R.I. 625½ Mµ) having a range of 0-12-½ microns.

EXAMPLE 5

In accordance with the procedurce of Example 3, a 2300 gram batch of a pigment paste composition was prepared using:

| | |
|---|---|
| Mill Base (Example 1) | 70.0% by weight |

| | |
|---|---|
| -continued | |
| D & C Red #7 Rosinated Ca. Lake | 30.0% by weight |

The three rolls of the Buehler SDX-600 mill were preheated to 106° F. and then rolls 1 and 3 were cooled to 97° F. The hydraulic roll pressure was set at 18.5 Bars (272 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by grind gauge used in Example 4.

EXAMPLE 6

The procedure of Example 3 was repeated in preparing a 2300 gram batch of a pigment paste composition using:

| | |
|---|---|
| Mill Base (Example 1) | 70.0% by weight |
| D & C Yellow #5 Zirconium Lake | 30.0% by weight |

The three rolls of the Buehler SDX-600 mill were preheated to 99° F. and then rolls 1 and 3 were cooled to 90° F. The hydraulic roll pressure was set at 16.5 Bars (243 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 7

The procedure of Example 3 was repeated in preparing a 2300 gram batch of a pigment paste composition using:

| | |
|---|---|
| Mill Base (Example 1) | 45.0% by weight |
| D & C TiO$_2$ | 55.0% by weight |

The three rolls of the Buehler SDX-600 mill were preheated to 80° F. and then rolls 1 and 3 were cooled to 72° F. The hydraulic roll pressure was set at 16 Bars (235 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 8

The procedure of Example 3 was repeated in preparing a 2300 gram batch of a pigment paste composition using:

| | |
|---|---|
| Mill Base (Example 1) | 56.0% by weight |
| Cosmetic Oxide M | 44.0% by weight |

The three rolls of the Buehler SDX-600 were preheated to 99° F. and then rolls 1 and 3 were cooled to 90° F. The hydraulic roll pressure was set at 16.5 Bars (243 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 9

The procedure of Example 3 was repeated in preparing a 2300 gram batch of a pigment paste composition using:

| | |
|---|---|
| Mill Base (Example 1) | 70.0% by weight |
| D & C Red #34 Ca. Lake | 30.0% by weight |

The three rolls of the Buehler SDX-600 mill were preheated to 99° F. and then rolls 1 and 3 were cooled to 90° F. The hydraulic roll pressure was set at 15 Bars (220 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 10

The procedure of Example 3 was repeated in preparing a 2300 gram batch of a pigment paste composition using:

| | |
|---|---|
| Mill Base (Example 1) | 55.0% by weight |
| D & C Red #6 Ba. Lake | 45.0% by weight |

The three rolls of the Buehler SDX-600 mill were preheated to 106° F. and then rolls 1 and 3 were cooled to 97° F. The hydraulic roll pressure was set at 18.5 Bars (272 lbs.). The hydraulic knife pressure was set a 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 11

The procedure of Example 3 was repeated in preparing a 2300 gram batch of a pigment paste composition using:

| | |
|---|---|
| Mill Base (Example 1) | 77.0% by weight |
| Cosmetic Ferric Blue F | 23.0% by weight |

The three rolls of the Buehler SDX-600 mill were preheated to 88° F. and then rolls 1 and 3 were cooled to 79° F. The hydraulic roll pressure was set at 15 Bars (220 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 12

The procedure of Example 3 was repeated in preparing a 2300 gram batch of a pigment paste composition using:

| Mill Base (Example 1) | 70.0% by weight |
| D & C Yellow #6 Al. Lake | 30.0% by weight |

The three rolls of the Buehler SDX-600 mill were preheated to 99° F. and then rolls 1 and 3 were cooled to 90° F. The hydraulic roll pressure was set at 15 Bars (220 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 13

The procedure of Example 3 was repeated in preparing a 2300 gram batch of a pigment paste composition using:

| Mill Base (Example 1) | 69.879% by weight |
| D & C TiO2 | 1.408% by weight |
| D & C Red #34 Ca. Lake | 26.924% by weight |
| Cosmetic Ferric Blue F | 1.789% by weight |

The three rolls of the Buehler SDX-600 mill were preheated to 99° F. and then rolls 1 and 3 were cooled to 90° F. The hydraulic roll pressure was set at 16.5 Bars (243 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 14

The procedure of Example 3 was repeated in preparing a 2300 gram batch of a pigment paste composition using:

| Mill Base (Example 1) | 48.520% by weight |
| Cosmetic Ferric Blue F | .200% by weight |
| D & C Red #6 Ba. Lake | 1.729% by weight |
| D & C TiO2 | 44.969% by weight |
| Cosmetic Iron Oxide M | 3.216% by weight |
| D & C Yellow #5 Zr. Lake | 1.366% by weight |

The three rolls of the Buehler SDX-600 mill were preheated to 127° F. and then rolls 1 and 3 were cooled to 118° F. The hydraulic roll pressure was set a 18.5 Bars (272 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 15

The procedure of Example 3 is repeated in the preparation of a 1000 gram batch of a pigment paste composition using:

| Mill Base (Example 2A) | 62.5% by weight |
| D & C Red #7 Ca. Lake | 37.5% by weight |

The three rolls of a Buehler SDX-600 mill are preheated to 99° F. and the rolls 1 and 3 are cooled to 97° F. The hydraulic pressure is set at 18.5 Bars (272 lbs.). The hydraulic knife pressure is set at 7 Bars (103 lbs.). The pigment slurry is passed three times through the mill at the above conditions to obtain a pigment paste composition having an average pigment particle size ranging from about 0.1 to about 2.0 microns as measured by the grind gauge used in Example 4.

EXAMPLE 16

The procedure of Example 3 is repeated in the preparation of a 1000 gram batch of a pigment paste composition using:

| Mill Base (Example 2D) | 70.0% by weight |
| D & C Yellow #5 Zr. Lake | 30.0% by weight |

The three rolls of a Buehler SDX-600 mill are preheated to 99° F. and then rolls 1 and 3 are cooled to 90° F. The hydraulic roll pressure is set at 16.5 Bars (243 lbs.). The hydraulic knife pressure is set at 7 Bars (103 lbs.). The pigment slurry is passed three times through the mill at the above conditions to obtain a pigment paste composition having an average pigment particle size ranging from about 0.1 to about 2.0 microns as measured by the grind gauge in Example 4.

It should be clear, from the foregoing, that the pigment composition is an intermediate product, ultimately to be incorporated into a lacquer formulation or similarly suitable vehicle for a coating composition e.g. nail polish. In accordance with the present invention and as a specific embodiment thereof, the disclosed pigment paste composition is combined with a lacquer formulation, to provide a novel and superior enamel coating composition containing a very high pigment level and having a low viscosity, heretofore unattainable with the prior art, nitrocellulose pigment chips.

The lacquer formulation of the present invention comprises a suitable primary film forming agent in combination with two modifying resins compatible therewith. Cellulose resins and particularly cellulose nitrate are preferred film forming agents, however, other suitable resins include: cellulose propionate, cellulose acetate butyrate, ethyl cellulose and acrylic resins, e.g. acrylic polymers (thermoplastic acrylic esters, homopolymers and copolymers of alkyl acrylates and methacrylates). Those skilled in the art will appreciate that various other ingredients present in either the lacquer formulation or the final composition may also act as film formers, e.g. the protective colloid used in the mill base, an amount of which will be carried into the final nail polish as part of the pigment paste.

The amount of the primary film forming agent present in the lacquer formulation generally ranges from about 10.0% to about 20.0%, with the preferred range being from about 11.0% to about 16.0% by weight.

The modifying resins present in the lacquer formulation must be compatible with the desired film forming agent. The primary role of the modifying resins is to impart gloss, to improve adhesion and to increase the hardness of the films. Suitable modifying resins include: toluene sulfonamideformaldehyde condensates; sucrose benzoate; sucrose acetate isobutyrate and copolymeric mixtures thereof. A preferred resin mixture comprises either Santolite MHP or Santolite MS-80 (80.0% solution) and Cellovar CV-160 (80.0% solution in butyl acetate) i.e., sucrose benzoate/sucrose acetate-isobutyrate copolymer.

The amount of the combined modifying resins present in the lacquer ranges from about 7.5% to about 18.0%, with the preferred range being from about 10.0% to 14.0%, based on 100% solids. Moreover, in the preferred resin mixture Santolite is present in an amount ranging from about 3.5% to about 7.0% and Cellovar CV160 is present in an amount ranging from about 4.0% to about 11.0%.

Surprisingly, it has been found that the combination of the modifying resins such as Santolite MHP and Cellovar CV160 when used in nail polish compositions containing very high pigment levels, e.g. at least above 2.0% pigment yields a composition having superior gloss, adhesion, wear and water resistant properties. In contrast thereto, the use of equivalent percentages of Santolite MHP in the high pigment nail polish formulations of the present invention generally result in soft, gummy films having unacceptable spectral gloss. Moreover, when the Santolite resin is present in amounts much greater than about 7.0%, the viscosity of the formulation is generally increased to a point where it becomes necessary to add a thinner, which while promoting commercially acceptable application properties, i.e. suitable brushability, adversely affects the solids and coverage properties of the final formulation. The use of equivalent percentages of Cellovar CV160 has been found to result in films which, while having a high gloss, are too brittle and generally exhibit unacceptable film flexibility. Although plasticizers may be added to overcome the brittleness problem, they tend to lengthen the drying time of the final formulations and cause the compositions to be easily smudged.

Accordingly, it has been found that a lacquer formulation comprising about 4.5% Santolite MHP and about 7.75% Cellovar CV160 (based on 100.0% solids) in combination with a suitable film former such as cellulose nitrate provides a superior lacquer formulation which when used with the pigment composition of the present invention produces a unique nail polish composition. Said polish has been found to exhibit the optimum film hardness and flexibility properties necessary for excellent wear resistance. The drying times, as well as the application properties are competitive with or superior to existing commercial nail polish compositions. The extremely high pigment levels which uniquely characterize the nail polish compositions of the present invention impart vastly superior color integrity and coverage properties, coat-for-coat, when compared with existing commercial nail polishes.

Optional ingredients present in the lacquer formulation include any and all ingredients well known in the art and conventionally employed in such formulations. Examples of such ingredients include plasticizers, e.g. see the list of plasticizers, supra; suspension agents, e.g. bentone clay; potentiating compounds which enhance the properties of suspension agents, e.g. malic acid; thinning agents, pearlescent agents, e.g. guanine and U.V. light stabilizers, e.g., Cyasorb 5411. It will be understood, however, that the use of particular ingredients in any specific lacquer formulation, of necessity, will be based upon the specific properties sought to be obtained in the final product.

The following is illustrative of a preferred, commercially available lacquer formulation and the general method of using the same in preparing a suitable final lacquer formulation.

A commercially available base lacquer, e.g. Isis Chemical Co.'s L1176, having the following formulation:

|  | % |
| --- | --- |
| ¼ sec. Cellulose nitrate 70% I.P.A. wet | 25.875 |
| ½ sec. Cellulose nitrate 70% I.P.A. wet | 6.480 |
| Butyl Acetate | 37.158 |
| Toluene | 18.579 |
| Isopropyl Alcohol | 2.538 |
| Santolite MHP | 9.370 |
|  | 100.000 | is combined with Bentone 27 Paste, Cellovar CV160, and Cyasorb 5411. The Bentone 27 Paste is prepared by placing thinner (75.0%) in a Cowles dissolver equipped with a covered change-can. The mixer is started and the Bentone 27 chips (25.5% Bentone, 18.0% camphor and 57.0% ¼ sec. dry cellulose nitrate) are slowly added. These materials are mixed under high shear conditions until the camphor and cellulose nitrate chips are dissolved and the Bentone is dispersed.

EXAMPLE 17

A 200 lbs. batch to a final lacquer formulation was prepared by weighing out 125.36 lbs. (62.68%) of the commercial base lacquer L1176; 47.96 lbs. (23.98%) Bentone 27 Paste; 26.44 lbs. (13.22%) Cellovar CV-160; and 0.24 lbs. (0.12%) Cyasorb 5411. These ingredients were placed in a covered tank equipped with a propeller mixer and thoroughly mixed at room temperature until dissolved and/or dispersed.

Examples 18–21, as shown in Table 1 below, are illustrative of other suitable lacquer formulations for use in accordance with the present invention.

TABLE 1

| Ingredients | % by weight | | | |
| --- | --- | --- | --- | --- |
|  | Ex. 18 | Ex. 19 | Ex. 20 | Ex. 21 |
| Nitrocellulose ¼ sec. RS | 8.90 | 9.32 | 13.00 | — |
| Nitrocellulose ½ sec. RS | 2.22 | 1.70 | — | — |
| Cellulose Acetate | — | — | — | — |
| Nitrocellulose 56 sec. dry | — | 1.00 | — | — |
| Ethyl Cellulose | — | — | — | 11.54 |
| Toluene | 21.60 | 13.91 | 17.50 | 43.95 |
| Cellovar CV160 (80.0% sol.) | 10.46 | 10.80 | 11.00 | 10.44 |
| Bentone paste (Ex. 17) | 18.93 | 19.30 | 20.45 | 18.68 |
| Santolite MS 80 (80.0% sol.) | 6.68 | 7.00 | — | — |
| Santolite MHP | — | — | 5.22 | 6.05 |
| Isopropyl alcohol | 3.62 | — | 5.68 | — |
| Ethyl acetate | 4.84 | 13.95 | 7.32 | — |
| Butyl acetate | 22.75 | 23.02 | 19.83 | — |
| Ethanol | — | — | — | 9.34 |
|  | 100.00 | 100.00 | 100.00 | 100.00 |

In preparing specific nail lacquer formulations those skilled in the art will appreciate that the amounts of ingredients compounded will be a function of the specific pigment shade chosen. For example, darker shades generally require a smaller pigment concentration than lighter shades in order to obtain satisfactory coverage properties. This caveat, notwithstanding, the following are general guidelines for preparing final nail polish formulations of the present invention.

EXAMPLE 22

The ingredients listed below are individually weighed out; transferred (in the order listed) into a suitable covered container equipped with a propeller-type mixer; and mixed until thoroughly dispersed:
  Santicizer 8
  Lacquer thinner
  Pigment paste Thereafter, a lacquer formulation, e.g. (Example 17) is weighed out and added to the above and thoroughly mixed. Finally, additional amounts of lacquer thinner may be added if necessary to adjust the viscosity of the composition and a suitable potentiating agent, e.g. malic acid, and guanine (22.0% dispersion) may also be added. The foregoing additives are mixed until thoroughly blended to provide a final nail lacquer composition. The sequence of the above processing steps including the preparation of the pigment paste are illustrated in the flow diagram shown in FIG. 1.

Examples 23 and 24 set forth two specific nail lacquer formulations which have been prepared in accordance with the above general guidelines. The pigment shades, black and pale lilac, were selected since they represent the extremes in pigment shades and the compositions prepared therefrom illustrate the range of preferred amounts (%) of the ingredients contained in all nail lacquer formulations having pigment shades which fall within the spectrum of colors between black and pale lilac.

EXAMPLE 23

Black Lacquer

| Ingredients | Parts | % by weight |
|---|---|---|
| Santicizer 8 | 1.7 | 1.43 |
| Guanine 22% dispersion | .4 | .34 |
| Pigment paste* | 12.0 | 10.13 |
| Thinner (44.0% butyl acetate; 13.0% ethyl acetate; 43.0% toluene) | 21.2 | 17.95 |
| L 1176 Base | 52.2 | 44.00 |
| Bentone 27 paste (25.5% solids) | 20.0 | 16.87 |
| Cellovar CV-160 | 11.0 | 9.28 |
| | 118.5 | 100.00 |

The percentage pigment present in the above formulation was 3.0493% based on the following:

| Pigment paste | | % by weight |
|---|---|---|
| Mill Base (Ex. 1) | | 7.0807 |
| D & C TiO₂ | 0.1427 | |
| D & C Red #34 Ca. Lake | 2.7274 | 3.0493 |
| Cosmetic Ferric Blue F | 0.1792 | |
| | | 10.1300 |

EXAMPLE 24

Pale Lilac

| Ingredients | Parts | % by weight |
|---|---|---|
| Santicizer 8 | 1.0 | .87 |
| Guanine 22% dispersion | .4 | .35 |
| Pigment paste* | 12.0 | 10.49 |
| Thinner (Ex. 24) | 17.8 | 15.57 |
| L 1176 Base | 52.2 | 45.63 |
| Bentone 27 paste (25.5% solids) | 20.0 | 17.48 |
| Cellovar CV-160 | 11.0 | 9.61 |
| | 114.4 | 100.00 |

The percent pigment present in the above formulation was 5.4004% based on the following:

| Pigment paste | | % by weight |
|---|---|---|
| Mill Base (Ex. 1) | | 5.0896 |
| D & C TiO₂ | 4.7173 | |
| Cosmetic Ferric Blue F | 0.0210 | |
| D & C Red #6 | 0.1814 | 5.4004 |
| Cosmetic Iron Oxide M | 0.3374 | |
| D & C Yellow #5 | 0.1433 | |
| | | 10.4900 |

The viscosity of the nail polish composition of Examples 23 and 24 (470 cps and 475 cps, respectively) as well as all compositions of the present invention does not exceed about 600 cps. This viscosity parameter is a Newtonian viscosity measured at 25° C. on a Brookfield viscometer Model LVT, No. 3 spindle with the spindle turning at 60 rpm. The viscosity measurements were all taken after vigorously agitating the nail polish composition in order to eliminate any thixotropic viscosity.

Table 2, set forth below, provides comparative data which illustrates the viscosity (Newtonian)/pigment load relationship between final nail polish compositions of the prior art and those prepared in accordance with the teaching of the present invention.

TABLE 2

| Ingredients | Parts | | | | | | | |
|---|---|---|---|---|---|---|---|---|
| | A | B | C | D | E | F | G | H |
| Lacquer formulation (Example 17) | 83.2 | 83.2 | 83.2 | 83.2 | 83.2 | 83.2 | 83.2 | 83.2 |
| Pigment Paste (Example 4) | 3.0 | — | 12.0 | — | 6.0 | — | 24.0 | — |
| Nitrocellulose Pigment Chip D & C Red #7 Ca. Lake Chip (prior art) | — | 3.0 | — | 12.0 | — | 6.1 | — | 24.4 |
| Thinner | 22.0 | 22.0 | 26.0 | 26.0 | 24.5 | 24.5 | 30.0 | 30.0 |
| Total Parts | 108.2 | 108.2 | 121.2 | 121.2 | 119.7 | 119.8 | 137.2 | 137.6 |
| % Pigment | 1.039 | 1.025 | 3.71 | 3.66 | 1.879 | 1.884 | 6.559 | 6.561 |
| Viscosity:* cps at 25° C. Brookfield Model LVT No. 3, spindle turning at 60 rpm. | 440 | 758 | 496 | 1012 | 490 | 778 | 470 | 3160 |

*Each composition was vigorously agitated for approximately 5 minutes before taking the viscosity reading.

In conducting the foregoing experiments, the identical lacquer formulation was used with both the pigment paste composition of the present invention and the prior art nitrocellulose pigment chip. D&C Red #7 Ca. Lake was selected as the pigment since the pigment concentration (%) of the chips and the paste of the present invention is a median figure for all shades, i.e. 37.0% pigment for the prior art nitrocellulose pigment chip and 37.5% pigment for the pigment paste. Formulations containing chips with lower pigment concentrations, e.g. D&C Red #34 Ca. Lake (20.0% pigment) would result in a greater viscosity increase since lower pigment concentrations require greater amounts of cellulose nitrate in formulating the chips, hence greater amounts of cellulose nitrate would be carried into the final formulation with the inevitable increase in viscosity. The reverse also holds true, i.e., higher pigment concentrations require lower concentrations of nitrocellulose; hence, lower viscosity. The same thinner adjustment was made to each set of formulations which contained an essentially identical percent concentration of solids.

Based on the data obtained from the four sets of experiments, it is apparent that at equivalent pigment and solids concentrations, the nail lacquers prepared in accordance with the present invention evidenced significantly lower viscosities than exhibited by the prior art formulations using the conventional nitrocellulose pigment chips. Even at lower pigment concentrations, i.e. A/B and E/F, the viscosities of the prior art compositions were nearly twice as great as the viscosities of the compositions of the present invention (440 vs. 758 and 490 vs. 778). Moreover, even at the lowest pigment concentration, i.e. experiment B (1.025% pigment), the formulation was found to exhibit unsatisfactory application properties and accordingly, it would be necessary to incorporate an additional amount of thinner to achieve desireable brushability. However, the resultant reduction in viscosity would also reduce the total solids (including the pigment and film former) and therefore, adversely affect the coverage properties of the composition. As is plainly evident from the data in Table 2, the increased pigment loads in experiments D (3.66%) and H (6.561%) result in even higher viscosities, i.e. 1012 and 3160 respectively and concomitantly even poorer and indeed totally unacceptable application properties.

It is, of course, to be understood that various modifications in the ingredients, proportions thereof and processing techniques and conditions disclosed hereinabove may be made without departing from the spirit and scope of the invention defined by the claims hereinbelow.

We claim:

1. A process for preparing high quality nail polish compositions comprising:
   grinding a pigment material in an essentially non-flammable, non-explosive mill base grinding medium comprising a water insoluble protective colloid and a low volatizing plasticizer in amounts sufficient to form a pigment dispersion paste;
   combining said pigment paste with a lacquer formulation containing sufficient amounts of a primary film forming material and modifying resins therefor; and
   mixing said pigment paste and lacquer formulation to provide a final, dermatologically acceptable nail polish composition having a pigment concentration of at least from to 2.0% to 7 by weight and a Newtonian viscosity of not greater than about 600 cps.

2. A process according to claim 1 wherein the pigment material is selected from the group consisting of a conventional single pigment; a single pearlescent; a mixture of a conventional single pigment and a single pearlescent; a mixture of conventional pigments; a mixture of pearlescents; and a mixture of conventional pigments and pearlescents.

3. A process according to claim 1 wherein the pigment dispersion paste is comprised of at least 20.0% by weight of the pigment material.

4. A process according to claim 1 wherein the protective colloid is compatible with the film forming material in the lacquer formulation and wherein the amount of said protective colloid is sufficient to coat the dispersed pigment particles with at least a monomolecular layer of said colloid to prevent said particles from agglomerating.

5. The process according to claim 4 wherein the protective colloid is selected from the group consisting of saccharide based polymers; acrylic polymers; polyesters; alkyd resins; polyamides; cellulosic polymers; sulfonated napthalenes; vinyl polymers; formaldehyde condensates; polyurethanes; substituted pyrrolidone polymers; and polypropylene oxides.

6. The process according to claim 5 wherein the protective colloid is selected from the group consisting of toluene sulfonamideformaldehyde condensate; methyl-butyl methacrylate copolymer; sucrose benzoate; ethyl cellulose; polymeric esterified pentaerythritol; and a dimer acid based polyamide resin.

7. The process according to claim 1 wherein the amount of the protective colloid present in the mill base ranges from about 2.0% to about 25.0% by weight of the mill base ingredients.

8. The process according to claim 1 wherein the plasticizer is essentially non-flammable, sufficiently solubilizes the protective colloid present in the mill base and is compatible with the film forming material present in the lacquer formulation.

9. The process according to claim 8 wherein the plasticizer is selected from the group consisting of N-ethyl toluene sulfonamide; butyl benzyl phthalate; and tricresyl phosphate.

10. The process according to claim 8 wherein the plasticizer is present in the mill base in amounts ranging from about 75.0% to about 98.0% by weight of the mill base ingredients.

11. The process according to claim 1 wherein the pigment material and mill base are milled under high energy shearing forces to provide a pigment dispersion paste having an average pigment particle size between about 0.1 to about 2.0 microns.

12. A process according to claim 1 wherein the film forming material present in the lacquer formulation is selected from the group consisting of cellulose resins and acrylic resins.

13. The process according to claim 12 wherein the film forming material is cellulose nitrate.

14. The process according to claim 12 wherein the film forming material is present in amounts ranging from about 10.0% to about 20.0% by weight of the lacquer formulation.

15. A process according to claim 1 wherein at least two modifying resins are present in the lacquer formulation.

16. A process according to claim 15 wherein the amount of modifying resins present in the lacquer formulation ranges from about 7.5% to about 18.0% by weight of the total lacquer ingredients.

17. A process according to claim 15 wherein the modifying resins are toluene sulfonamide-formaldehyde condensate and sucrose benzoate/sucrose acetate-isobutyrate copolymer.

* * * * *